(12) United States Patent
Kleinman et al.

(10) Patent No.: US 9,283,069 B2
(45) Date of Patent: Mar. 15, 2016

(54) INTRAVITREOUS SELF ADAPTIVE STENT

(71) Applicant: Empire Technology Development LLC, Wilmington, DE (US)

(72) Inventors: David Maxwell Kleinman, Rochester, NY (US); Trevor John Moody, Seattle, WA (US); Kenneth Eugene Perry, Jr., Bainbridge Island, WA (US)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 0 days.

(21) Appl. No.: 14/112,275

(22) PCT Filed: Mar. 15, 2013

(86) PCT No.: PCT/US2013/032104
§ 371 (c)(1),
(2) Date: Oct. 17, 2013

(87) PCT Pub. No.: WO2013/154762
PCT Pub. Date: Oct. 17, 2013

(65) Prior Publication Data
US 2014/0296976 A1    Oct. 2, 2014

Related U.S. Application Data

(60) Provisional application No. 61/624,060, filed on Apr. 13, 2012.

(51) Int. Cl.
A61F 2/14    (2006.01)
A61F 2/88    (2006.01)
A61F 9/007   (2006.01)
(Continued)

(52) U.S. Cl.
CPC ... *A61F 2/14* (2013.01); *A61F 2/16* (2013.01); *A61F 2/88* (2013.01); *A61F 9/00727* (2013.01); *A61L 31/022* (2013.01); *A61L 31/16* (2013.01);
(Continued)

(58) Field of Classification Search
CPC ..... A61F 9/00781; A61F 9/0017; A61F 2/14; A61F 2/16; A61F 2/147
USPC ................................. 623/4.1, 23.7
See application file for complete search history.

(56) References Cited

U.S. PATENT DOCUMENTS 4,800,882 A    1/1989   Gianturco
4,969,458 A    11/1990  Wiktor
(Continued)

FOREIGN PATENT DOCUMENTS

WO    WO-2011/097408    11/2011
WO    WO-2011/103555    12/2011

OTHER PUBLICATIONS

Ambati et al., "Postoperative complications of scleral buckling surgery," Int Ophthalmol Clin; 2000 Winter; 40(1); pp. 175-185.
(Continued)

*Primary Examiner* — Thomas J Sweet
*Assistant Examiner* — Tiffany Shipmon
(74) *Attorney, Agent, or Firm* — Foley & Lardner LLP

(57) ABSTRACT

An intravitreous stent includes a multi-loop single wire having a proximal end; a distal end; at least a first loop defined by the proximal end and a first portion of the single wire; at least a second loop defined by the distal end and a second portion of the single wire; wherein the first portion is joined to the second portion via a reversing loop portion.

21 Claims, 2 Drawing Sheets

(51) Int. Cl.
*A61F 2/16* (2006.01)
*A61L 31/02* (2006.01)
*A61L 31/16* (2006.01)

(52) U.S. Cl.
CPC . *A61F 2210/0014* (2013.01); *A61F 2230/0071* (2013.01); *A61F 2250/0003* (2013.01)

(56) References Cited

U.S. PATENT DOCUMENTS

| | | | |
|---|---|---|---|
| 5,342,387 | A | 8/1994 | Summers |
| 5,356,423 | A | 10/1994 | Tihon et al. |
| 5,545,210 | A | 8/1996 | Hess et al. |
| 5,562,641 | A | 10/1996 | Flomenblit et al. |
| 6,315,791 | B1 | 11/2001 | Gingras et al. |
| 6,451,052 | B1 | 9/2002 | Burmeister et al. |
| 6,699,285 | B2 | 3/2004 | Zapata |
| 6,758,858 | B2 | 7/2004 | McCrea et al. |
| 7,527,632 | B2 | 5/2009 | Houghton et al. |
| 7,658,761 | B2 | 2/2010 | Yamauchi et al. |
| 2003/0114916 | A1 | 6/2003 | Pinchasik |
| 2006/0052821 | A1* | 3/2006 | Abbott et al. ............ 606/213 |
| 2011/0172755 | A1 | 7/2011 | Nelson et al. |
| 2012/0035738 | A1 | 2/2012 | Dai |

OTHER PUBLICATIONS

Chang, "LXII Edward Jackson Lecture: Open angle glaucoma after vitrectomy," American Journal of Ophthalmology, Jun. 2006; 7; pp. 1033-1043.

International Search Report and Written Opinion for Intl. Pat. Appln. No. PCT/US2013/032104, mailed on Jul. 26, 2013, 10 pp.

Kim et al., "Postoperative complications of pneumatic retinopexy," Int Ophthalmol Clin, 2000 Winter; 40(1); pp. 165-173.

Krzystolik et al., "Complications of intraocular tamponade: Silicone oil versus intraocular gas," Int Ophthalmol Clin, 2000 Winter; 40(1); pp. 187-200.

Pandya et al., "Retinal Detachment," Medscape Reference; Sep. 2010; http://emedicine.medscape.com/articie/798501-overview, 5 pages.

Mitry et al., "Pathogenesis of Rhegmatogenous retinal detachment: Predisposing anatomy and cell biology," Retina; Nov.-Dec. 2013; 30(1); pp. 1561-1572.

Ocampo et al., "Senile cataract," Medscape Reference; Mar. 2012; http://emedicine.medscape.com/article/1210914-overview#a0199.

Olson et al., "Ocular biocompatibility of nitinol intraocular clips," Invest Ophthalmol Vis Sci; Jan. 2012; 53(1); pp. 354-360.

Pastor et al., "Proliferative vitreoretinopathy: risk factors and pathology," Prog Ret Eye Res; Jan. 2002; 21(1); pp. 127-144.

Puustjarvi et al., "Retinal fixation of traumatic retinal detachment with metallic tacks: A case report with 10 years' follow-up," Retina; Feb. 2001; 21(1); pp. 54-56.

Schaal et al., "Primary retinal detachment repair: Comparison of 1-year outcomes of four surgical techniques," Retina; Sep. 2011; 31(8); pp. 1500-1504.

Sodhi et al., "Recent trends in the management of rhegmatogenous retinal detachment," Surv of Jan.-Feb. 2008; 53(1); pp. 50-67.

Wagenfeld et al., "Long-lasting endotamponades in vitreoretinal surgery," Ophthalmologica; Mar. 2010; 224; pp. 291-300.

* cited by examiner

INTRAVITREOUS SELF ADAPTIVE STENT

CROSS-REFERENCE TO RELATED APPLICATIONS

The present application is a U.S. national stage application claiming the benefit of International Application No. PCT/US 2013/032104, filed on Mar. 15, 2013, which in turn claims the benefit of priority to U.S. Provisional Patent Application No. 61/624,060, filed on Apr. 13, 2012, both of which are incorporated herein by reference in their entirety for any and all purposes.

BACKGROUND

Proliferative vitreoretinopathy (PVR) is a catastrophic complication of a retinal detachment (RD) and can cause profound visual loss. PVR is a scar tissue formation within the eye and is typically treated by surgeries.

Treatment for PVR includes, but is not limited to, e.g., pars plana vitrectomy, membrane peeling where small instruments are used to peel the membranes from the surface of the retina, and scleral buckling. These techniques are combined with fluids placed in the eye to flatten the retina and reattach it to the outer wall of the retina followed by laser photocoagulation to connect the retina permanently. Typically, the fluids used are perfluoron (PFO) or perfluoro-n-octane which are heavier-than-water fluid and push the retina into its normal position. When injected, PFO settles to the back of the eye and pushes the subretinal fluid to the front. Alternatively, a gas bubble is placed in the eye to hold the retina in place while it is healing, or as another alternative, silicone oil is used to hold the retina in its position. Disadvantages of the gas bubble include, but are not limited to, that the patient must restrict the movement of their head for two to three weeks following surgery before they can go back to normal activities. Disadvantages of the silicone oil bubble include, but are not limited to, that the patient requires removal of the oil in several months following the procedure. Additional disadvantages of both the gas bubble and the silicone bubble include that these techniques may lead to secondary glaucoma and may not be effective to inferior retina.

More than 500,000 vitrectomy surgeries are performed annually in the world. About 80% of surgeries are performed with temporary tamponade, such as gas, silicone oil or heavy silicone oil of which about 10% surgeries are not successful. There is a need for efficient and simple treatment of eye diseases related to retinal detachment.

SUMMARY

In one aspect, a intravitreous stent is provided, the stent including a multi-loop single wire having a proximal end, a distal end, at least a first loop defined by the proximal end and a first portion of the single wire, at least a second loop defined by the distal end and a second portion of the single wire, and wherein the first portion is joined to the second portion via a reversing loop portion. In some embodiments, the proximal end, the distal end, or both the proximal end and the distal end include a curled feature. In any of the above embodiments, the stent is self adaptive to a dimension of a vitreous cavity in the eye. In any of the above embodiments, the second loop is configured to form to an equator of a vitreous cavity of an eye. In any of the above embodiments, the proximal end is configured to reside within the anterior chamber of an eye. In any of the above embodiments, configured to retain a detached retina in an eye.

In any of the above embodiments, the single wire includes a shape memory substance. In any of the above embodiments, the singe wire includes a titanium-nickel (Ti—Ni) based alloy. In some such embodiments, the Ti—Ni based alloy has about 43.5 wt % to about 52 wt % Ti and about 48 wt % to about 56.5 wt % Ni. In some embodiments, the Ti—Ni based alloy has about 44 wt % Ti and about 55.6 wt % Ni. In some other embodiments, the Ti—Ni based alloy comprises a Ti—Ni—X alloy where X is at least one of Fe, V, Cr, Co, or Nb. In some such embodiments, the Ti—Ni based alloy comprises about 43.5 wt % to about 51 wt % Ti, about 40 wt % to about 56.5 wt % Ni, and about 0 wt % to about 9 wt % X. In any of the above embodiments, X may be Nb.

In any of the above embodiments, the stent may further include a fixation point for fixing the stent in an eye. Alternatively, or in addition, the stent may further include one or more projections configured for grasping of the stent or fixing the stent in an eye. The one or more projections may include one or more regions in the stent which are configured to receive a suture.

In any of the above embodiments, the second loop may include a sinusoidal wave configured to perpendicularly contact a retina of an eye, such that one or more zenith points or nadir points of the sinusoidal wave are configured to contact the retina.

In any of the above embodiments, the proximal end of the stent may include a projection for fixing a natural or synthetic intraocular lens within an eye.

In another aspect, a method is provided for inserting an intravitreous stent into an eye, the method including inserting a cannula through an anterior portion of an eye, and feeding an intravitreous stent through the cannula and into the eye; wherein: the intravitreous stent includes a multi-loop single wire having a proximal end; a distal end; at least a first loop defined by the proximal end and a first portion of the single wire; and at least a second loop defined by the distal end and a second portion of the single wire; and wherein the first portion is joined to the second portion via a reversing loop portion. The method may further include positioning the intravitreous stent with the second loop at approximately an equator of an intravitreous cavity of the eye and the proximal end in the anterior portion of the eye. Any of the methods may include positioning the intravitreous stent within the eye. Any of the methods may also include re-positioning the intravitreous stent within the eye.

In another aspect, an intravitreous stent is provided including an inflatable, ring-shaped balloon having an inflation mechanism, wherein, the balloon includes a polymer. The intravitreous stent may be configured to form to an equator of an intravitreous cavity.

In another aspect, a method for securing a natural or synthetic intraocular lens in an eye is provided, the method including inserting a cannula through an anterior portion of an eye; and feeding an intravitreous stent through the cannula and into the eye; contacting a natural or synthetic intraocular lens with the intravitreous stent to fix a position of the lens within the eye; wherein: the intravitreous stent includes a multi-loop single wire having a proximal end; a distal end; at least a first loop defined by the proximal end and a first portion of the single wire; at least a second loop defined by the distal end and a second portion of the single wire; and wherein the first portion is joined to the second portion via a reversing loop portion.

In another aspect, a method of treating an ocular disease in a subject is provided, the method including implanting any intravitreous stent as described above, wherein: the intravitreous stent is self adaptive to a dimension of a vitreous cavity in the eye, thereby treating the ocular disease in the subject. In one embodiment, the intravitreous stent supports a detached retina or proliferative membrane near an equator of the eye. In another embodiment, the method includes suturing the intravitreous stent to scleral tissue at pars plana of a ciliary body in the eye. In such methods, the ocular disease may be vitreoretinopathy.

In another aspect, a method is provided for treating vitreoretinopathy in a subject, the method including implanting any of the described intravitreous stents in an eye of the subject, where the stent is self adaptive to a dimension of a vitreous cavity in the eye and secures the retina.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
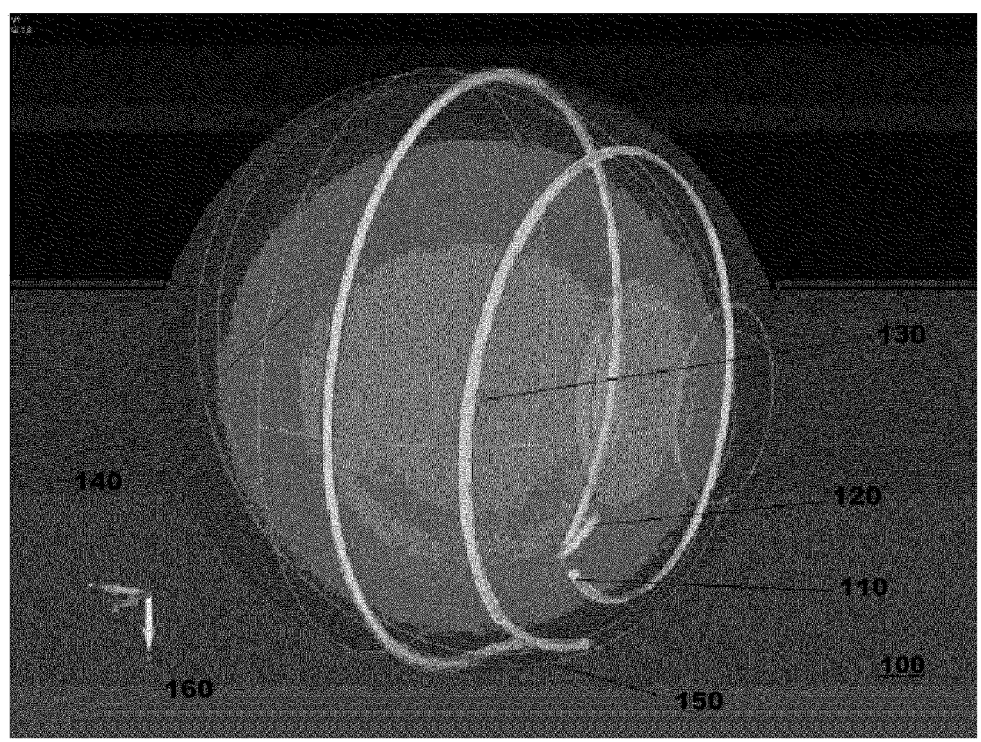
FIG. 1 is an illustration of an intravitreous stent disposed within an eye, according to one embodiment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

The present technology is described herein using several definitions, as set forth throughout the specification. As used herein, unless otherwise stated, the singular forms "a," "an," and "the" include plural reference.

The term "comprising" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude trace contaminants from the isolation and purification method and pharmaceutically acceptable carriers, such as phosphate buffered saline, preservatives and the like. "Consisting of" shall mean excluding more than trace elements of other ingredients and substantial method steps for administering the compositions of this technology or process steps to produce a composition or achieve an intended result. Embodiments defined by each of these transition terms are within the scope of this technology.

In one aspect, an intravitreous stent is provided for treating an eye. The intravitreous stent includes a multi-loop single wire. The wire has a proximal end and a distal end. The proximal and distal ends of the wire are arbitrarily assigned and may be reversed. The wire also has a first loop which is defined by the proximal end of the wire and a first portion of the wire, and a second loop which is defined by the distal end of the wire and a second portion of the wire. The first and second portions of the wire are joined by a reversing loop. As used herein, a reversing loop is a bend in the wire which provides for the first and second loops to be positioned in similar relative rotation to one another.

For example, FIG. 1 is an illustration of an intravitreous stent 100 described above. The intravitreous stent 100 includes a first loop defined by the proximal end 110 and the first portion 130, and the second loop defined by the distal end 120 and second portion 140. As will be noted at an intermediary point between the proximal end 110 and the distal end 120, the reversing loop 150 provides for the first loop and the second loop to both extend from the reversing loop to their respective ends in a similar clockwise rotation. Had the first and second loops been continuously formed without a reversing loop, the portions of the loop from the intermediary point extending to the respective end, would have extended in clockwise and counterclockwise rotations.

The intravitreous stents are self adaptive to a dimension of a vitreous cavity in the eye. For example, the second loop of the stent is configured to form to the equator of the vitreous cavity in the eye. The second loop is also configured to provide an outward spring force to secure a retina to the interior of the eye, if the retina is detached or is at risk of becoming detached. The dimension of the vitreous cavity may vary depending on the species, gender or age of the subject. For example, the vitreous cavity of a child or an infant is smaller than the vitreous cavity of an adult subject.

The first loop is configured to also be positioned in the vitreous cavity of an eye, or is configured to at least partially reside within the anterior cavity of the eye. By being placed at least partially within the anterior cavity, the first loop may provide for additional securement of the retina, or it may provide a fixation point for a dislodged or dislocated intraocular lens. In some embodiments, it is the proximal end of the wire that resides within the anterior cavity.

In order to provide contact between the wire and the retina, without excessive contact that could otherwise damage retinal ganglion tissue, the second portion of the wire, i.e. the portion defined by the reversing loop and the distal end, may be formed into a sinusoidal wave. The sinusoidal wave is formed such that the wave is perpendicular to the retina when the wire is in position within the vitreous cavity of an eye. This allows for the zenith or nadir points of the sinusoidal wave to contact the retina, while the remaining ascending and descending portions of the wave are not in contact with the retina. Other wave forms or shapes will be readily apparent which provided for minimal retinal touch points along the length of the wire without impacting the integrity of the wire. One illustrative example would be a square wave.

Figure 2:
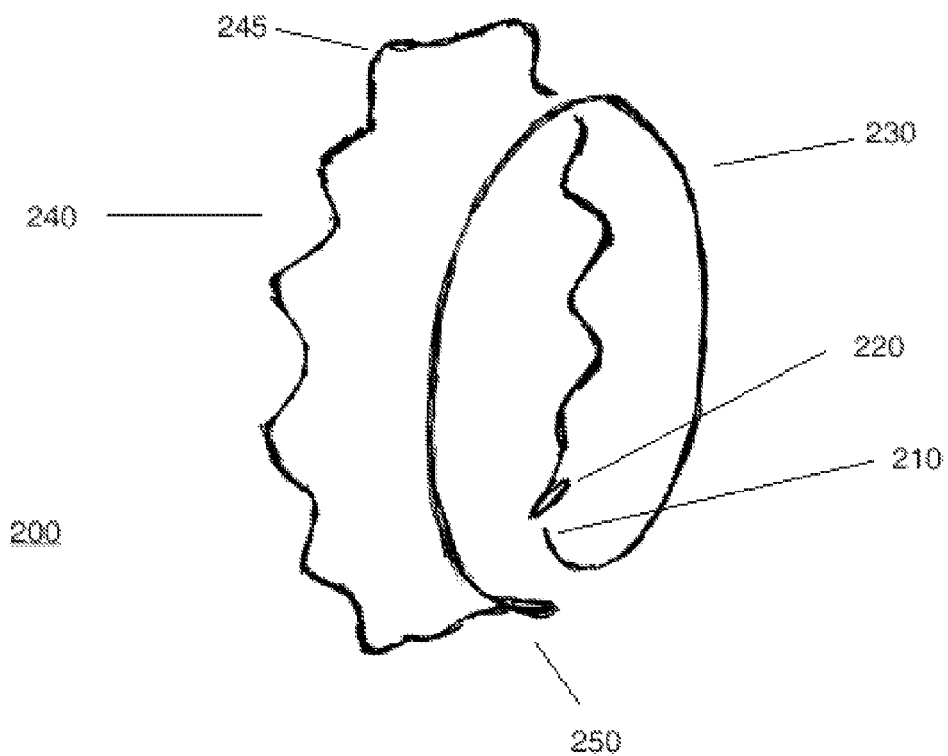
FIG. 2 is an illustration of an intravitreous stent having a sinusoidal wave in the wire, according to one embodiment.

An illustrative example of the sinusoidal wave intravitreous stent 200 is shown in FIG. 2. The intravitreous stent 200 includes a first loop defined by the proximal end 210 and the first portion 230, and the second loop defined by the distal end 220 and second portion 240. As will be noted at an intermediary point between the proximal end 210 and the distal end 220, the reversing loop 250 provides for the first loop and the second loop to both extend from the reversing loop to their respective ends in a similar clockwise rotation. The second portion 240 of the stent includes a sinusoidal wave form having zenith (or nadir, depending on the viewers perspective) points 245 which contact the retina or inner surface of the eye in the vitreous cavity. Thus, the sinusoidal wave of the second portion 240 is approximately perpendicular to the inner eye surface which the wire contacts, such that the zenith or nadir points 245 of the wire contact the inner eye surface, thus minimizing contact.

The proximal, distal, or both proximal and distal ends of the wire may contain a feature which eases an otherwise blunt or sharp end of the wire. For example, one or both of the ends may contain a curled loop or bend, as illustrated in FIG. 1. A curled end feature on the proximal end may also be used to engage a dislodged or dislocated intraocular lens to retain it in its position, or prevent it from becoming dislodged or dislocated further.

The intravitreous stent may include features, or fixation points, which allow for the stent to be secured or fixed to the eye using a suture. Accordingly, projections from the stent may be present which allow for a suture connection, or one or more apertures may be included along a length of the stent through which a suture may be threaded and secured. Such projections may also be used for grasping by tools to position the stent within the eye.

In an alternative embodiment, an intraocular lens may be attached to the intravitreous stent, which is then attached to the eye. Such a stent with an attached intraocular lens can be used to treat eyes which either need an intraocular lens or need a replacement of the existing intraocular lens in addition to vitreoretinopathy. The lenses may be natural lenses that are native to the eye undergoing treatment, or as a transplanted lens from another eye. The lenses may also be synthetic lenses replacing the eye's natural lens. The intravitreous stent may be used to fix or secure a dislodged or dislocated lens within the eye in its proper position, or prevent further dislodgement or dislocation of a lens which has had some movement from its proper position. In one illustrative embodiment, the intravitreous stent would not only provide the intraocular lens to the subject but would also attach to the retina of the eye of the subject.

The intravitreous stent may be made from any shape memory material. This is because the stent is to be inserted into an eye through a cannula. Although such a cannula may be curved, in order to provide for the looping of the wire inside the eye, the stent must self-assume the multi-looped form after passing through the cannula into the eye. Thus, prior to, or during, insertion in the eye, portions of the stent may be subjected to forces which cause the loops to straighten, however after insertion, the loops must reform without, or with only minimal, exterior manipulation.

Illustrative shape memory materials include, but are not limited to, titanium-nickel (Ti—Ni) alloys. The Ti—Ni alloy is an alloy that remembers its original, cold, forged shape (martensite phase), or which returns to that shape after being deformed by applying heat (austenitic or parent phase). The shape memory alloy, such as a Ti—Ni alloy, exhibits a remarkable shape memory effect in association with martensitic reverse transformation and exhibits spontaneous shape recovery and spring characteristics (superelasticity) in a parent phase region after the reverse transformation from a martensite region. Accordingly, the Ti—Ni alloy may be formed into the intravitreous stent at manufacture or prior to insertion into an eye (i.e. an original shape). During insertion into the eye, the intravitreous stent may undergo mechanical forces that disturbs the original shape. For example, as described the stent may be inserted into the eye through a cannula. Although the cannula may be curved to some extent, the full curvature of the stent is not likely to be exactly conformed to by the cannula. Therefore, some straightening of the stent within the cannula may occur, or in the case of a stent having an at least partial sinusoidal wave shape, the wave may be compressed or straightened when passing through the cannula. However, upon release of the mechanical forces (for example, emerging from the cannula in the examples of the previous sentences), the Ti—Ni alloy stent may then return to the original shape either merely from release of the mechanical forces, or in response to a change in temperature from outside the eye to within the eye.

In one embodiment, the Ti—Ni shape memory alloy is characterized in that, at a temperature above a reverse transformation finish temperature (Af point) at which reverse transformation of the alloy starting from a reverse transformation start temperature (As point) is finished, the alloy that has been deformed under an external load is recovered into an original shape simultaneously when the external load is released. Herein, the As point means a shape recovery start temperature while the Af point means a shape recovery finish temperature (shape recovery temperature). The alloy has the Af point not substantially lower than a living body temperature (approximately 37° C., or as appropriate for the animal or mammal or life stage).

In some embodiments of the present technology, the Ti—Ni based alloy includes about 43.5 wt % to about 52 wt % Ti, and about 48 wt % to about 56.5 wt % Ni. In some embodiments, the Ti—Ni alloy includes about 44 wt % Ti and about 55.6 wt % Ni. In some embodiments, the Ti—Ni based shape memory alloy comprises Ti at about 45 wt % and Ni at about 55 wt %. In some embodiments, the Ti—Ni based shape memory alloy comprises Ti at about 44 wt % and Ni at about 56 wt %. In some embodiments, the Ti—Ni based shape memory alloy comprises Ti at about 43.5 wt % and Ni at about 56.5 wt %. In some embodiments, the Ti—Ni based shape memory alloy comprises Ti at about 46 wt % and Ni at about 54 wt %. Individual values within the above ranges are also included such that the Ti and Ni amounts correspond to one another to 100 wt %. Nitinol is one example of a commercially available Ti—Ni alloy.

In some embodiments, the Ti—Ni alloy is a Ti—Ni—X alloy, where X is at least one selected from iron (Fe), vanadium (V), chromium (Cr), cobalt (Co), and niobium (Nb). In some embodiments, the Ti—Ni alloy includes Ti, Ni, and Fe. In some embodiments, the Ti—Ni alloy includes Ti, Ni, and V. In some embodiments, the Ti—Ni alloy includes Ti, Ni, and Cr. In some embodiments, the Ti—Ni alloy includes Ti, Ni, and Co. In some embodiments, the Ti—Ni alloy includes Ti, Ni, and Nb.

In some embodiments, the Ti—Ni alloy is a Ti—Ni—X—Y alloy where X is at least one selected from iron (Fe), vanadium (V), chromium (Cr), cobalt (Co), or niobium (Nb) and Y is at least one selected from copper (Cu) or zirconium (Zr). In some embodiments, the Ti—Ni alloy is a Ti—Ni—X—Y—Z alloy where X is at least one selected from iron (Fe), vanadium (V), chromium (Cr), cobalt (Co), or niobium (Nb); Y is copper (Cu); and Z is zirconium (Zr).

In some embodiments, the Ti—Ni—X based alloy includes Ti at about 43.5 wt % to about 51 wt %, Ni at about 40 wt % to about 56.5 wt %, and X at 0 wt % to about 9 wt %. In some embodiments, the Ti—Ni—X alloy includes Ti at about 43.5 wt % to about 51 wt %, Ni at about 40 wt % to about 56.5 wt %, and Fe, V, Cr, Co, or Nb at 0 wt % to about 9 wt %. In some embodiments, the Ti—Ni—X—Y—Z alloy includes Ti at about 43.5 wt % to about 51 wt %; Ni at about 40 wt % to about 56.5 wt %; Fe, V, Cr, Co, or Nb at 0 wt % to about 5 wt %; and Cu and/or Zr at 0 wt % to about 4 wt %.

The intravitreous stent may optionally include a coating of a therapeutic agent, which may delivered to the vitreous cavity or anterior cavity of an eye upon deployment of the intravitreous stent within the eye. In some embodiments, the therapeutic agent is mixed in a polymeric matrix before being coated onto the stent. A coating, typically of a polymer, may hold and elute (release) the therapeutic agent into the eye by contact transfer. Examples of such polymers include, but are not limited to, poly-n-butyl methacrylate and polyethylene-vinyl acetate copolymer or poly(lactide-co-Σ-caprolactone) copolymer. The coating may be designed to biodegrade after or as the drug is eluted. Coatings may typically be spray coated or dip coated by dipping the stent into the polymer. There can be one to three, or more, layers in the coating e.g. a base layer for adhesion, a main layer for holding the agent, and optional top coat to slow down the release of the drug and extend its effect.

The therapeutic agent may be any agent known in the art that can be administered to the eye. In some embodiments, the therapeutic agent is an anti-proliferative agent, neuron protective agent, antibiotic, anti-inflammatory agent, glaucoma drug, anti-viral agent, anti-allergy agent, or a mixture of any two or more such agents.

VEGF is responsible for the growth of new blood vessels. It promotes this growth by stimulating the endothelial cells, which form the walls of the vessels and transport nutrients and oxygen to the tissues. When the retinal pigment epithelial (RPE) cells begin to wither from lack of nutrition (a condition called "ischemia"), the VEGF goes into action to create new vessels. This process is called neovascularization, and it acts as a restorative function in other parts of the body. In the retina, however, the vessels do not form properly, and leaking results. This leakage causes scarring in the macula and eventual loss of central vision.

Anti-proliferative agents or anti-VEGF agents prevent the VEGF from binding with the receptors on the surface of the endothelial cells. Neovascularization is then blocked, preventing bleeding into the retina. Examples of anti-proliferative drugs include, but are not limited to, actinomycin, colchicine, cytosine arabinoside hydrochloride, 5-fluorodeoxyuridine, vinblastine sulfate, daunomycin, Macugen® (pegaptanib sodium), Lucentis® (ranibizumab), Tryptophanyl-tRNA synthetase (TrpRS), AdPEDF, VEGF-Trap-Eye, Avastin® (bevacizumab), Sirolimus® (rapamycin), and endostatin.

A neuronal death can be a result of episodes of anoxia and ischaemia in the retina and other eye diseases, such as anterior ischemic optic neuropathy, glaucoma etc. The neuronal death can be due to the accumulation of glutamate in the extracellular space. Glutamate is the primary excitatory neurotransmitter in the retina. However, excessive over-activation of glutamate receptors can lead to excitotoxic neuronal cell death. Glutamate excitotoxicity can also cause neuronal mitochondrial membrane potential (MMP) loss, which is associated with changes in mitochondrial function leading to a neuronal dysfunction. Ginkgo biloba extract 761 (EGb761) is a standardized extract of the Ginkgo biloba. EGb761 is an example of a neuron protective agent that has a neuro-protective effect in many nervous system diseases, such as neuro-degenerative diseases, anoxia and ischemia, and peripheral nerve damage. Another example of neuron protective agent is a nerve growth factor (NGF). The "nerve growth factor" or "NGF" refers to any biologically active form of NGF, such as, but not limited to, e.g., NGF β-subunit, either natural or recombinant, hybrid or modified forms of NGF that bind to their corresponding receptor and preserve the bioavailability of NGF, or NGF fragments or hybrids in which some amino acids have been eliminated or substituted, on condition that the resulting product maintains a sufficient capacity to bind to the specific receptor.

Antibiotics are generally used to treat, or sometimes to prevent a bacterial eye infection. Examples of antibiotics include, but are not limited to, vancomycin, cephalosporins, sulfacetamide, erythromycin, gentamicin, tobramycin, ciprofloxacin, ofloxacin, or combination thereof.

Anti-inflammatory agent can reduce inflammation, which in the eye is usually manifested by pain, redness, light sensitivity and blurred vision. Examples of anti-inflammatory agents include, but are not limited to, corticosteroids such as triamcinolone acetonide, prednisolone, fluorometholone, or dexamethasone; and non-steroids such as, diclofenac, ketorolac, or flurbiprofen, or combination thereof.

Glaucoma medications attempt to reduce the eye's intraocular pressure, the fluid pressure inside the eye, to prevent damage to the optic nerve resulting in loss of vision. These medications may lower pressure by decreasing the amount of fluid produced in the eye, by increasing the amount of fluid exiting through the eye's natural drain, or by providing additional pathways for fluid to leave the eye. Examples of glaucoma drugs include, but are not limited to, betablockers such as, timolol, metipranolol, carteolol, betaxolol, or levobunolol; alpha agonists, such as, brimonidine or iopidine; prostaglandin analogues, such as, latanoprost; carbonic anhydrate inhibitors, such as dorzolamide; cholinergic agonists, such as, pilocarpine or carbachol; and adrenergic agonists, such as, epinephrine or dipivefrin, or combination thereof.

Typically used in treating herpes virus infections of the eye, cytomegalovirus or human Immunodeficiency virus, anti-viral eye medications may be used in conjunction with oral medications for elimination the virus. Examples of anti-virals include, but are not limited to, ganciclovir, acyclovir, valaciclovir, triflurthymidine, adenine arabinoside or idoxuridine.

The anti-allergy agents decrease the effects of histamine which creates itching, swelling, redness, and watering in the eye. They may work either by preventing the release of histamine in the body or by blocking its effect after it is released. Examples of anti-allergy agents include, but are not limited to, livostin, patanol, cromolyn, alomide or pheniramine.

In some embodiments, the therapeutic agent in the stent is released as an immediate release of the agent or a controlled release of the agent. In some embodiments, the therapeutic agent is coated or attached or embedded in the stent along with one or more of excipients suitable for eye. Such excipients are well known in the art and some of the examples include, but are not limited to, sodium hyaluronate, taurine (or 2-aminoethanesulphonic acid), vitamin E, vitamin A, cytidine-5'-diphosphate choline (CDP-choline), etc.

Various methods for making the stent are well known in the art. The stents can be manufactured by methods, such as, but not limited to, laser welding, sputter deposition, wet etching, etc.

Methods

In one aspect, a method is provided for inserting an intravitreous stent into an eye. The method includes inserting a cannula through an anterior portion of an eye and feeding any of the about intravitreous stents through the cannula and into the eye. Upon insertion of the wire through the cannula the wire deforms, however as the wire emerges from the cannula inside the eye, the shape memory alloy re-assumes its original shape with the second loop configured to contact the equator of the vitreous cavity and the first loop configured to be within the anterior cavity of the eye. The method may further include positioning the intravitreous stent in the eye with the second loop at approximately the equator of the vitreous cavity. The method may also include observing the positioning of the stent within the eye and re-position if necessary to obtain a preferred contact between the stent and the retina in the case of treating a detached or detaching retina.

The terms "treating," "treatment" and the like refer to obtaining a desired pharmacologic and/or physiologic effect. The effect can be prophylactic in terms of completely or partially preventing a disease or disorder or sign or symptom thereof, and/or can be therapeutic in terms of a partial or complete cure for a disorder and/or adverse effect attributable to the disorder. Examples of "treatment" include, but are not limited to, e.g., preventing a disease from occurring in a subject that may be predisposed or at risk of a disease, such as retinal detachment, but has not yet been diagnosed as having it; inhibiting a disease, i.e., arresting its development; and/or relieving or ameliorating the symptoms of disease or reducing the likelihood of recurrence of the disease, such as retinal detachment or vitreoretinopathy. As is understood by those skilled in the art, "treatment" can include systemic amelioration of the symptoms associated with the pathology and/or a delay in onset of symptoms.

The ocular disease includes any disorder associated with a retinal detachment in the eye. There are various types of retinal detachments, including, but not limited to, rhegmatogenous retinal detachment; exudative, serous, or secondary retinal detachment; and tractional retinal detachment. The rhegmatogenous retinal detachment may occur due to a hole, tear, or break in the retina that may allow fluid to pass from the vitreous space into the subretinal space between the sensory retina and the retinal pigment epithelium. The exudative, serous, or secondary retinal detachment may occur due to inflammation, injury or vascular abnormalities that may result in fluid accumulating underneath the retina without the presence of a hole, tear, or break. The tractional retinal detachment may occur when fibrovascular tissue, caused by an injury, inflammation or neovascularization, pulls the sensory retina from the retinal pigment epithelium.

Other illustrative disorders of the eye such as, but are not limited to, inflammation, allergy, virus, infection, glaucoma, neuronal death, anterior ischemic optic neuropathy, neurodegenerative diseases, anoxia and ischemia, peripheral nerve damage, pain, redness, light sensitivity, blurred vision, and the like are treated along with ocular disease as defined above. These other disorders are treated by the therapeutic agent attached or embedded or coated on the stent, as described herein.

The methods include treatment of a patient population that shows symptoms or signs of retinal detachment. Such symptoms include, but are not limited to, e.g., flashing lights, floaters, and a shadow or curtain that affects any part of the vision. Retinal detachments may be associated with congenital malformations, metabolic disorders, trauma (including previous ocular surgery), glaucoma, vascular disease, choroidal tumors, high myopia or vitreous disease, or degeneration. As noted above, PVR is a disorder that is associated with a retinal detachment in the eye. PVR can occur posteriorly and/or anteriorly with folding of the retina both anteriorly and circumferentially. PVR can be divided into multiple categories based on the configuration of the retina and the location of the scar tissue, and this categorization may be used by eye care specialists to describe the severity and configuration of the retina in PVR.

In some embodiments, any of the intravitreous stents described above is implanted into the vitreous cavity of the eye. The stent adapts to the dimension of the vitreous cavity of the eye and comes into contact with the detached retina. The stent prevents further detachment of the retina and restores the shape of the retina. In some embodiments, the stent supports a detached retina or proliferative membrane near the equator of the eye. In some embodiments, the stent supports a detached retina or proliferative membrane anterior to an equator of the eye.

In some embodiments, the stent is introduced into a vitreous cavity of the eye by insertion through a cannula in an anterior portion, or on the sclera of the eye. The term "implantation" or "implanting," refers to the delivery of a stent to an appropriate location of the subject or in vitro, where a desired effect is needed. In some embodiments, the introduction of the stent into the eye further comprises suturing the stent to sclera at the pars plana of ciliary body in the eye.

In one aspect of the present technology, there is provided a method of treating vitreoretinopathy in a subject, by inserting an intravitreous stent in an eye of the subject.

In some embodiments, the implantation of the stent as in the present technology, demonstrates advantages, such as, but not limited to, biocompatibility, reduced number of follow up surgeries, reduced recovery time, reduced time for bed rest, and reduced or no recurrence of retinal detachment.

In another aspect, an intravitreous stent is provided, the stent including an inflatable, ring-shaped balloon. The balloon includes an inflation mechanism such that once the uninflated balloon is inserted into the vitreous cavity of an eye, the balloon may be inflated via the inflation mechanism to contact an area approximating the equator of the vitreous cavity and secure the retina to the interior of the eye. This balloon stent will provide for a significant amount of surface area of the balloon to contact the retina. This provides for a lower pressure requirement and potentially minimal damage to the retinal ganglion tissue.

The inflation mechanism may be self activated or activated by external manipulation. For example, the inflation mechanism may be an attachment to which a pump is connected to inflate the balloon. Alternatively, the inflation mechanism may include a self inflating mechanism or gas producing material that is activated once the balloon is place within the vitreous cavity.

The balloon may be constructed with a polymer. The polymer allows for the collapsing of the stent into a small package that may be inserted into the vitreous cavity of an eye where the balloon is then inflated. The polymer may be a biodegradable or bioresorbable polymer such that after the stent has secured the retina and the retina has had sufficient time to reattach to the interior of the eye, the polymer may biodegrade or bioresorb into the eye or subject. Such biodegradable or bioresorbable polymers do not require subsequent removal. In other embodiments, the polymer may be non-biodegradable or non-bioresorbable. Such non-biodegradable or non-bioresorbable polymers may be used in applications where it is not anticipated that the retina will reattach to the eye or where the detachment of the retina is such that use of a biodegradable or bioresorbable stent is not practical.

As used herein, "biodegradable" refers to a material that breaks down into smaller fragments by the natural environment. Such fragments may be surgically removed, or may be small enough that the body removes them. As used herein, "bioresorbable" or "bioabsorbable" refers to a material that is broken down into the body and absorbed by the body.

Illustrative polymers that may be used in the construction of the balloon may include, but are not limited to, silicon, styrene, polypropylene, polyurethane, and polytetrafluoroethylene, a polyester, a polyethyleneoxide, a polymethacrylate, or a polyacrylic acid. For example, the polymer may include an aliphatic ester C1-C50 of acrylic acid or a methacrylic acid ester of polyethyleneoxide. In some embodiments, the aliphatic ester C1-C50 of acrylic acid is an aliphatic ester C1-C50 of methacrylic acid. For example, the polymer may be prepared from monomers such as butyl acrylate, polyacrylic acid, pentafluoropropylacrylate, polyethylene glycol methacrylate, polyethyleneglycol monomethylether methacrylate, methylmethacrylate, poly(methyl methacrylate), isobornyl methacrylate, isobutyl methacrylate, perfluoroacetylmethacrylate, tertiary butylmethacrylate, phenylethylmethacrylate, hydroxyethyl methacrylate, glycerol methacrylate, and heptadecylfluorodecyl-methacrylate. In some embodiments of the balloon, the polymer is poly(methyl methacrylate), polyacrylic acid, or a poly(hydroxyethyl) methacrylate. In some embodiments of the balloon, the flexible material of the stent is the methacrylic acid ester of polyethyleneoxide which includes, but is not limited to, polyethyleneglycol dimethacrylate, polyethyleneglycol methacrylate or polyethyleneglycol acrylate.

In some embodiments, the polymer is a biodegradable material. Examples of such biodegradable materials include, but are not limited to, poly(caprolactone-β-ethylene oxide) or poly(L-lactide-co-glycolide). Such biodegradable materials suitable for the stent of the present technology are well known in the art and are well within the scope of the present technology. In some embodiments, the biodegradable material degrades in the eye within the period of from about 1 week to about 5 years; or alternatively within the period of from about 2 week to about 3 years; or alternatively within the period of from about 2 week to about 2 years; or alternatively with in the period of from about 2 week to about 1 year; or alternatively with in the period of from about 2 week to few months.

In some embodiments, the balloon is biologically compatible. The term "biologically compatible" is intended to refer to a material that does not substantially react with the human body and does not cause any substantial allergic reaction. By "substantial," it is intended that the material does not cause a reaction that is beyond the tolerable limits of the subject or the reaction subsides after a few hours or days.

In some embodiments, the balloon may include a therapeutic agent. The therapeutic agent may be any of those as are described above. In some embodiments, the therapeutic agent is coated onto the balloon either directly or in a polymer matrix to provide for a delayed release. In some embodiments, the therapeutic agent is mixed with the polymer that forms the balloon to elute from the balloon over time. Examples of polymers to provide for delayed release include, but are not limited to, poly-n-butyl methacrylate and polyethylene-vinyl acetate copolymer or poly(lactide-co-Σ-caprolactone) copolymer. The coating may be designed to biodegrade after or as the drug is eluted. Coatings may typically be spray coated or dip coated by dipping the balloon into the polymer. There can be one to three or more layers in the coating e.g. a base layer for adhesion, a main layer for holding the agent, and optional top coat to slow down the release of the drug and extend its effect.

Methods

In one aspect, the present technology provides a method of treating an ocular disease in a subject, by implanting an intravitreous stent, which includes that balloon, in an eye of the subject. The stent is composed of a flexible material, and the stent is self adaptive to a dimension of a vitreous cavity in the eye.

Kits

In one aspect, the present technology provides a kit comprising any of the above intravitreous stents for treating an eye. The kits may further include suitable packaging and/or instructions for use of the stent. Kits may also comprise a means for the delivery of the stent, such as syringe, catheter, or other such devices. The kits may further include surgical tools.

The kits may also include other compounds for use in conjunction with the stent(s). Such compounds include, but are not limited to, e.g., alcohol, analgesics, anesthetics, antiseptics, etc. These compounds can be provided in a separate form. The kits may include appropriate instructions for implantation of the stent, side effects, and any other relevant information. The instructions can be in any suitable format, including, but not limited to, e.g., printed matter, videotape, or computer readable disk.

EQUIVALENTS

The present disclosure is not to be limited in terms of the particular embodiments described in this application. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a member being from 1 cm to 4 cm also includes the member being 2 cm or 3 cm.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. An intravitreous stent comprising:
   a multi-loop single wire comprising:
      a proximal end;
      a distal end;
      at least a first loop defined by the proximal end and a first portion of the single wire;
      at least a second loop defined by the distal end and a second portion of the single wire, wherein the second loop comprises a sinusoidal wave configured to perpendicularly contact a retina of an eye, such that one or more zenith points or nadir points of the sinusoidal wave are configured to contact the retina;
   wherein:
      the first portion is joined to the second portion via a reversing loop portion;
      the second loop has a diameter that is larger than that of the first loop; and the intravitreous stent is self adaptive to a dimension of a vitreous cavity in an eye;

and wherein the stent is configured to be straightened prior to or during insertion in the eye.

2. The intravitreous stent of claim 1, wherein the proximal end, the distal end, or both the proximal end and the distal end comprise a curled feature.

3. The intravitreous stent of claim 1, wherein the second loop is configured to form to an equator of a vitreous cavity of an eye.

4. The intravitreous stent of claim 1, wherein the proximal end is configured to reside within the anterior chamber of an eye.

5. The intravitreous stent of claim 1 configured to retain a detached retina in an eye.

6. The intravitreous stent of claim 1, wherein the single wire comprises a shape memory substance.

7. The intravitreous stent of claim 1, wherein the single wire comprises a titanium-nickel (Ti-Ni) based alloy.

8. The intravitreous stent of claim 7, wherein the Ti-Ni based alloy comprises about 43.5 wt % to about 52 wt % Ti and about 48 wt % to about 56.5 wt % Ni.

9. The intravitreous stent of claim 7, wherein the Ti-Ni based alloy comprises a Ti-Ni-X alloy where X is at least one of Fe, V, Cr, Co, or Nb.

10. The intravitreous stent of claim 9, wherein the Ti-Ni based alloy comprises about 43.5 wt % to about 51 wt % Ti, about 40 wt % to about 56.5 wt % Ni, and about 0wt % to about 9 wt % X.

11. The intravitreous stent of claim 1 further comprising a fixation point for fixing the stent in an eye.

12. The intravitreous stent of claim 1 further comprising one or more projections for grasping or fixing of the intravitreous stent, wherein the projections comprise one or more regions in the stent configured to receive a suture.

13. The intravitreous stent of claim 1, further comprising a therapeutic agent.

14. The intravitreous stent of claim 13, wherein the therapeutic agent is an anti-proliferative drug, a neuron protective drug, an antibiotic, an anti-inflammatory, a glaucoma drug, an anti-viral, or an anti-allergy agent.

15. The intravitreous stent of claim 1, wherein the proximal end comprises a projection for fixing a natural or synthetic intraocular lens within an eye.

16. A method of treating an ocular disease in a subject, comprising:

implanting an intravitreous stent according to claim 1 in an eye of the subject; wherein: the intravitreous stent is self adaptive to a dimension of a vitreous cavity in the eye, thereby treating the ocular disease in the subject.

17. The method of claim 16, further comprising suturing the intravitreous stent to scleral tissue at pars plana of a ciliary body in the eye.

18. The method of claim 16, wherein the ocular disease is vitreoretinopathy.

19. A method for securing a natural or synthetic intraocular lens in an eye, the method comprising:

inserting a cannula through an anterior portion of an eye;

feeding an intravitreous stent through the cannula and into the eye; and contacting a natural or synthetic intraocular lens with the intravitreous stent to fix a position of the lens within the eye;

wherein: the intravitreous stent comprises:

a multi-loop single wire comprising:

a proximal end;

a distal end;

at least a first loop defined by the proximal end and a first portion of the single wire;

at least a second loop defined by the distal end and a second portion of the single wire, wherein the second loop comprises a sinusoidal wave configured to perpendicularly contact a retina of an eye, such that one or more zenith points or nadir points of the sinusoidal wave are configured to contact the retina; and wherein:

the first portion is joined to the second portion via a reversing loop portion;

the second loop has a diameter that is larger than that of the first loop; and the intravitreous stent is self adaptive to a dimension of a vitreous cavity in an eye;

and wherein the stent is configured to be straightened prior to or during insertion in the eye.

20. The method of claim 19 further comprising inserting a natural or synthetic intraocular lens into the eye.

21. The method of claim 19, wherein the lens is a dislocated natural lens and the intraocular stent fixates the lens from further dislocation.

* * * * *